United States Patent [19]

Halm

[11] 4,153,769

[45] May 8, 1979

[54] VINYL POLYMERIZATION WITH BORON CHELATES AS CATALYST AND PHOTOCONDUCTIVE SENSITIZER

[75] Inventor: James M. Halm, Lombard, Ill.

[73] Assignee: A. B. Dick Company, Niles, Ill.

[21] Appl. No.: 739,651

[22] Filed: Nov. 8, 1976

[51] Int. Cl.$^2$ .......................... C08F 4/14; C08F 30/06
[52] U.S. Cl. .................................. 526/195; 96/1 PC; 260/340.7; 427/74; 526/196; 526/263; 526/346
[58] Field of Search ............... 526/195, 196, 238, 258, 526/259, 263, 346; 260/340.7

[56] References Cited

U.S. PATENT DOCUMENTS

| | | | |
|---|---|---|---|
| 3,155,503 | 11/1964 | Cassiers | 260/895 |
| 3,679,637 | 7/1972 | Hort | 526/259 |
| 3,957,732 | 5/1976 | Hirooka | 526/196 |
| 4,007,317 | 2/1977 | Sirotkina | 526/259 |

*Primary Examiner*—C. A. Henderson
*Attorney, Agent, or Firm*—McDougall, Hersh & Scott

[57] ABSTRACT

The preparation of a photoconductor which comprises the polymerization reaction product of an N-alkenyl carbazole or derivative thereof such as N-vinyl carbazole, in the presence of a catalyst in the form of a monochelate or muli-chelate of boron in which the chelate catalyzes the polymerization reaction and remains in the polymerization product as a sensitizer for the photoconductive properties of the organic polymer.

11 Claims, No Drawings

VINYL POLYMERIZATION WITH BORON CHELATES AS CATALYST AND PHOTOCONDUCTIVE SENSITIZER

This invention relates to the polymerization of vinyl monomers to form homopolymers and copolymers and particularly vinyl carbazoles and derivatives thereof with boron chelates and to photoconductive compositions and elements produced therewith.

BACKGROUND OF THE INVENTION

Poly-N-vinyl carbazoles and derivatives thereof are substances widely used as organic photoconductors in the preparation of electrostatic photoconductive elements from which multiple copies can be produced in the duplicating field. By themselves, the poly-N-vinyl carbazoles and derivatives are not sufficiently photoconductive unless modified by the presence of varying amounts of acceptor type compounds, such as fluorenone derivatives, phthalic anhydride derivatives, halogenanil derivatives or ketone derivatives. In practice, the electron affinitive compound (acceptor compound) is blended with the polymer after polymerization of the carbazole monomers.

N-vinyl carbazole and its derivatives polymerize very slowly in the absence of a polymerization catalyst. For purposes of accelerating polymerization use has been made of a catalyst such as ditertiary butyl peroxide, azobisbutyronitrile, betanaphthol, monoethyl aluminum dichloride, and the like. The presence of such catalysts in the polymer often presents problems in the subsequent formation of the charge transfer complex or interferes in other ways with the selected acceptor. As a result, it has been the common practice to remove the catalyst from the polymer before formulating the polymer with the desired electron affinitive compound, if the polymer is to be used as a photoconductor. Such separation steps are costly and time consuming and thus introduces a barrier to the commercial acceptance of photoconductive elements fabricated of such organic photoconductors.

SUMMARY OF THE INVENTION

It is an object of this invention to provide a method for producing a polyalkenyl-carbazole and derivatives thereof, such as poly-N-vinyl carbazole, by polymerization of the monomer in the presence of a catalytic agent which is sufficiently electro-negative to result in a photoconductive material which can be used in the preparation of photoconductive elements, and it is a related object to produce and to provide a method for producing new and novel ketonate compounds which find utility in the polymerization to produce new and improved photoconductive polymers of alkenyl carbazoles and derivatives thereof.

It has been found, in accordance with the practice of this invention, that a class of compounds, heretofore referred to as initiators, are effective to catalyze the polymerization of alkenyl carbazoles and derivatives thereof, and more particularly N-vinyl carbazole, wherein the resulting polymerization products are sufficiently electro-negative to enable the catalytic component to remain in the formed polymer composition to produce an organic photoconductive material in which a high degree of photoconductivity may be achieved by comparison with the mere blend of the catalyst compound with a polymerized N-vinylcarbazole. The new class of compounds have the following general formula:

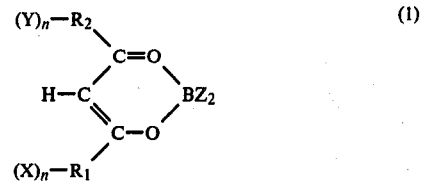

in which X and Y may be the same or different and represents a alkyl group having from 1 to 10 carbon atoms, such as methyl, ethyl, propyl, isopropyl, cyclopropyl, butyl, isobutyl, cyclobutyl, pentyl and the like, or an aryl or alkaryl groups, such as phenyl, tolyl, anthracyl and the like, and an alkoxy group, such as methoxy, ethoxy and the like, or halogenated methyl derivative, such as methyl chloride; Z is phenyl or a halogen group such as chloro, but preferably fluoro, n is a number of from 1 to 5 and $R_1$ and $R_2$ may be the same or different, and are represented by an alkyl group having from 1 to 10 carbon atoms as defined above, or an aryl or alkaryl group as defined above. Included are the group of compounds in which $R_2$ is represented by the group having the general formula

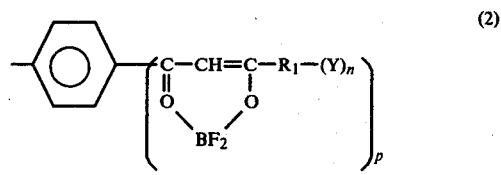

in which $R_1$ has the same meaning as defined above and p is a number of from 1 to 2.

The following structural formulae illustate preferred initiator compounds produced in accordance with the practice of this invention and embraced within the above structural formulae:

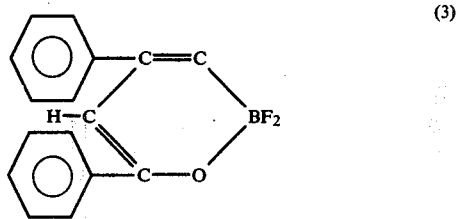

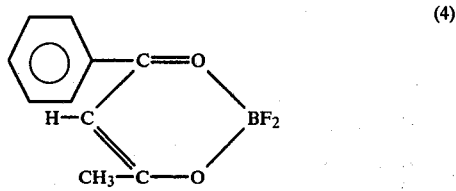

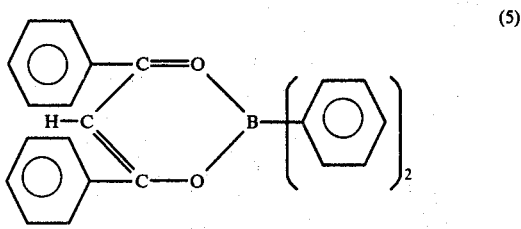

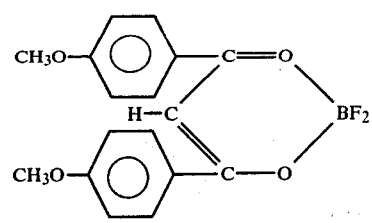 (6)

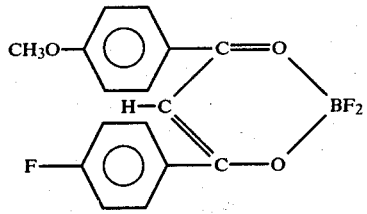 (7)

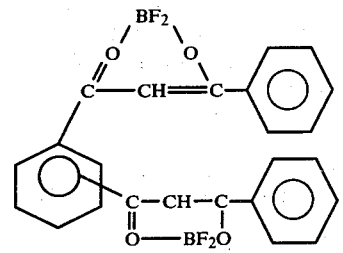 (8)

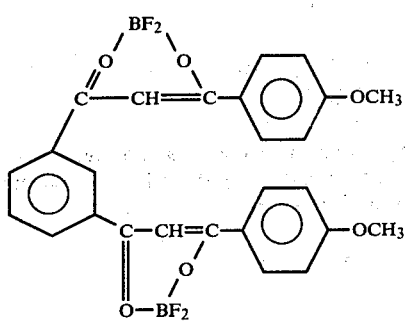 (9)

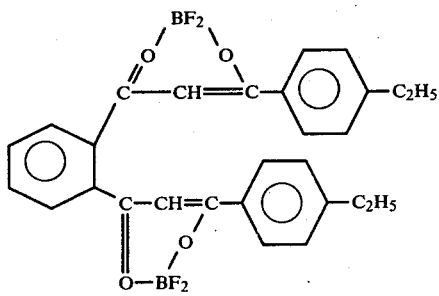 (10)

In the practice of this invention, the initiator is intimately mixed with the carbazole monomer and then heated until fusion of the mixture occurs, while in an inert atmosphere such as a blanket of nitrogen. The mixture is heated for reaction at a temperature generally within the range of 65°–160° C., with agitation.

The amount of initiator used to catalyze the polymerization reaction will depend somewhat upon the reaction temperature, the individual components reacted, the amount desired in the final product, and the solubility of the initiator in the melt. A desirable effect is achieved when use is made of the initiator in an amount of 0.5% by weight of the monomer. Beneficial use is derived from additional amounts of initiator but it is undesirable to make use of an amount which exceeds 20% by weight of the monomer. In practice, it is preferred to make use of initiator in an amount within the range of 1.0 to 4.0% by weight of the monomer. Within this range, the desired amount of polymerization can be achieved at temperatures within the range of 60°–200° C. For example, with 1.5% by weight catalyst, polymerization is completed in 30 minutes at 80° C. and with 3.0% by weight catalyst, polymerization is completed in 15 minutes at 80° C.

Polymerization by an amount suitable for use in the preparation of photoconductive coatings is indicated by increase in viscosity of the melt and/or by an abrupt darkening of the melt which normally coincides with increase in viscosity or solidification of the reaction mass.

The polymerization reaction mass can be taken up in a solvent, such as hot tetrahydrofuran, to form a coating composition which can be applied to a suitable substrate, preferably a conductive substrate paper, metal, plastics and the like, as by dip coating, draw rod coating, or the like, followed by drying and preferably curing at elevated temperature. Coatings having a thickness of 3 to 12 microns are sufficient and it will be seen that the coating strongly bonds to the surface of the substrate.

In my copending application Ser. No. 897,719, filed Apr. 19, 1978, as a continuation-in-part of application Ser. No. 737,148, filed Oct. 29, 1976, now abandoned and entitled "Photoconductive Coating and Composition", description is made of the manufacture of monochelates represented by the equations (1) to (5). The monochelates have heretofore been produced but use thereof has not been made as polymerization catalysts.

Multi-chelates, as represented by the structural formula (2) and illustrated by the formulae (6) to (8), are believed to be new and novel compounds which have not heretofore been produced and their use as catalysts in the polymerization of N-vinyl carbazoles and derivatives thereof in the production of new and improved photoconductive materials is also believed to be new.

Such multi-chelates can be produced, in accordance with the practice of this invention, by reaction of the appropriate ligand with a BF$_3$ etherate, as illustrated by the following examples.

PREFERRED EMBODIMENTS OF THE INVENTION

EXAMPLE 1

(a) Preparation of ligand.

The ligand is first prepared by a Cross Claisen condensation reaction of dimethyl terephthalate with 4'-ethylacetophenone in accordance with the following equation

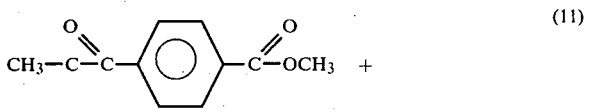 (11)

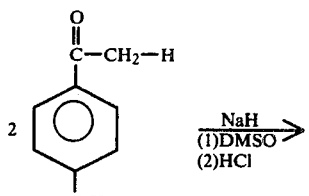

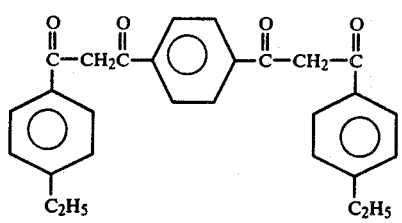

A 200 ml portion of dimethyl sulfoxide is placed over 15 grams of sodium hydride (50% in oil) and the mixture is stirred for about one-half hour. Approximately 0.2 mol (39 g) of dimethyl terephthalate is added to the sodium hydride and the mixture stirred for about one-half hour under a nitrogen atmosphere which is maintained by passing nitrogen through a bobbler. A portion of 0.4 mol (59 g) of 4'-ethylacetophenone is added to an equal volume of dimethyl sulfoxide and the solution is added dropwise, from a dropping funnel, to the stirred mixture of sodium hydride and acetone. An ice water bath is used to control the temperature of the reaction mixture when it begins to foam and reflux due to the exothermic reaction. After completion of the addition of ketone, the mixture is stirred at room temperature for 5 hours. The red mixture is poured into a beaker (1 liter) half filled with ice and containing 100 ml of concentrated HCl. The yellow precipitate is isolated by filtration and dissolved in 400 ml $CH_2Cl_2$. The $CH_2Cl_2$ solution is washed with a 200 ml portion of sodium bicarbonate and then twice with 200 ml portions of water. The $CH_2Cl_2$ solution is evaporated on a steam bath to one-third its original volume and the solution placed in a freezer at about 31 10° C. over night.

The yellow solid from the crystallization was used in the preparation of the boron chelate.

(b) Preparation of chelate.

The chelated compound was obtained by reaction of the tetraketone ligand with $BF_3$ etherate in accordance with the following equation:

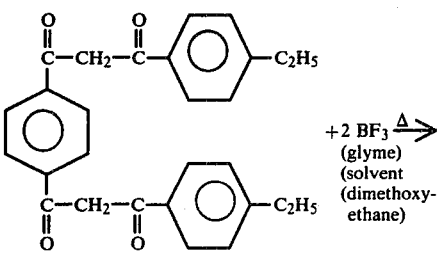

(12)

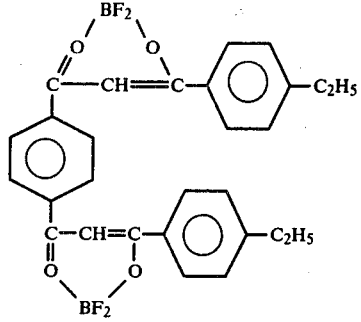

20 grams (0.048 mol) of the ketone was added to about 200 ml of 1,2-dimethoxyethane solvent and the mixture was stirred under a nitrogen atmosphere. The mixture was brought to about 50° C. and 12.6 grams of a 50% $BF_3$ (as the ethyl etherate) (0.096 mol) was added to the mixture. The suspension was refluxed for 4 hours, cooled and then filtered.

The yellow-orange solid was re-crystallized from hot acetone as fractions from a Soxhlet extractor. The third fraction, after about 48 individual extractions of the solid, was taken for analysis as product and used for the catalysis reaction and as a blend sensitizer in the formed polymerization product.

EXAMPLE 2

In the preparation of the dichelate, represented by the formula (7), the 4-ethylacetoxyphenone in Example 1 was replaced by an equal amount of 4'-methylacetophenone.

EXAMPLE 3

In the preparation of the compound represented by the formula (6), Example 1 was followed except that the 4'-ethylacetophenone was substituted by an equivalent amount of acetophenone.

The following examples, which are given by way of illustration, and not by way of limitation, demonstrate the use of the boron chelates as catalysts in the polymerization of N-vinylcarbazole and derivatives for the preparation of organic polymers having improved photoconductive characteristics.

EXAMPLE 4

10 grams of N-vinylcarbazole are thoroughly mixed with 0.3 gram of the compound represented by the formula (5) and placed in a flask containing a stirrer button. The flask is flushed out with a nitrogen stream for 10 minutes and a nitrogen atmosphere is maintained by continued bubbling of nitrogen therethrough. The flask is heated until the mixture melts at a temperature of about 60°–65° C. Polymerization is continued for 10 minutes with corresponding increase in viscosity and resultant color change from a yellow to a deep amber. The mass quickly solidifies. The reaction mass is etracted with hot tetrahydrofuran (THF), a slight residue filtered off, and the volume of solution adjusted to 100 ml with THF.

The solution is coated onto an aluminum substrate with a draw rod. The tough adhesive film, formed upon drying, was transparent and had high photopic transmission. Its electrophotoconductive properties, when illuminated from a tungsten light source, were as follows:

1. positive charge acceptance=460 volts, dark decay=1.9 volts/sec., exposure required to t1/3 of the decay curve=330 μj/cm, residual voltage=50 volts.

2. negative charge acceptance=600 volts, dark decay=1.7 volts/sec., exposure required to t1/3 of the decay curve=360 μj/cm, residual voltage=40 volts.

EXAMPLE 5

The same procedure was carried out with the same substances as in Example 4 except that the ratio of initiator/monomer=0.9 g/10 g. The melt solidified in a few seconds. A drawbar coating from 100 ml of THF gave the following electrophotoconductive properties when illuminated by a tungsten light source:

1. postive charge acceptance=500 volts, dark decay=16.6 volts/sec., exposure required to t1/3 of the decay curve=144 μJ/cm$^2$, residual voltage=50 volts.

2. negative charge acceptance=550 volts, dark decay=8 volts/sec., exposure to t1/3 of the decay curve=187 μJ/cm$^2$, residual voltage=30 volts.

The THF was evaporated off from the solution of Example 4, and mixed solvent THF/cyclohexanone=40/60 (%) was used as the coating solvent. With the use of either solvent, the coating was transparent and of high photopic transmission. From the mixed solvent, the electrophotoconductive properties of a drawbar coating, with tungsten illumination, were:

1. positive acceptance=400 volts, dark decay=18 volts/sec., exposure required to t1/3 of the decay curve=216 μj/cm$^2$, residual voltage=30 volts.

2. negative charge acceptance=400 volts, dark decay=19 volts/sec., exposure to t1/3 of the decay curve=291 μJ/cm$^2$, residual voltage=30 volts.

EXAMPLE 6

The procedure of Example 4 was followed except that the compound (5) was replaced with the compound represented by the formula (6), and the ratio of initiator/monomer=0.3 g/10 g. The melt solidified after about 15 minutes at 80° C. The reaction mass was extracted into the THF and the final solution was diluted to 100 ml in a solvent system of 60/40 THF/cyclohexanone. A tough transparent film with excellent adhesion on an aluminum substrate was obtained. The film, with high photopic transmission, had the following electrophotographic properties:

1. positive charge acceptance=420 volts, dark decay=1 volt/sec., exposure required to t1/3 of the decay curve=396 μj/cm$^2$, residual voltage=30 volts.

2. negative charge acceptance=410 volts, dark decay=1 volt/sec., exposure required to t1/3 of the decay curve=480 μJ/cm$^2$, residual voltage=40 volts. A readable copy was made from this photoconductive plate from a commercial copy machine using negative corona.

EXAMPLE 7

The procedure of Example 4 was followed except that use was made of the initiator represented by the formula (7) in the ratio initiator/monomer=0.15 g/5.0 g. Polymerization took place about 10 minutes after the mixture melted with the temperature near 80° C. The reaction product, dissolved in THF, was coated onto an aluminum substrate and formed a tough adhesive, transparent film. The electrophotographic properties of this coating, with the use of tungsten illumination, were:

1. postive charge acceptance=500 volts, dark decay=6.6 volts/sec., exposure to t1/3 of the decay curve=2205 μJ/cm$^2$, residual voltage=100 volts.

2. negative charge acceptance=650 volts, dark decay=4 volts/sec., exposure to t1/3 of the decay curve=2200 μJ/cm$^2$, residual voltage=40 volts.

EXAMPLE 8

The procedure of Example 4 was followed except that the initiator was the compound represented by formula (9) with the ratio initiator/monomer=0.4 g/10 g. The melt polymerized after about 10 minutes at 80° C. The reaction mass was extracted into hot THF and the volume concentrated to 100 ml. The particulate matter was filtered off and the solution coated onto an aluminum substrate. A tough, adhesive, transparent film of high photopic transmission was obtained having the following electrophotographic properties toward tungsten illumination:

1. positive charge acceptance=850 volts, dark decay=3 volts/sec., exposure required to t1/3 of the decay curve=141 μJ/cm$^2$, residual voltage=50 volts.

2. negative charge acceptance=790 volts, dark decay=1 volt/sec., exposure to t1/3 of the decay curve=206 μJ/cm$^2$, residual voltage=50 volts.

EXAMPLE 9

The procedure of Example 8 was repeated with the same substances but in the ratio initiator/monomer=0.8 g/10 g. The reaction mass polymerized in a few seconds after the melt formed. The THF coating on an aluminum substrate exhibited the physical properties as in Example 8. The electrophotographic properties of this coating toward tungsten illumination were:

1. positive charge acceptance=650 volts, dark decay=6 volts/sec., exposure required to t1/3 of the decay curve=91 μJ/cm$^2$, residual voltage=50 volts.

2. negative charge acceptance=700 volts, dark decay=3 volts/sec., exposure to t1/3 of the decay curve=139 μJ/cm$^2$, residual voltage=50 volts. When an 80B filter was to simulate more of a daylight fluorescent quality, the electrical proprties were:

1. positive acceptance=600 volts, dark decay=6 volts/sec., exposure to t1/3 of the decay curve=81 μJ/cm$^2$, residual voltage=50 volts.

2. negative charge acceptance=650 volts, dark decay=4 volts/sec., exposure to t1/3 of the decay curve=181 μJ/cm$^2$, residual voltage=50 volts.

Excellent line copy was obtained when a plate coated with this polymerization formulation was used in a commercial copy machine employing positive corona.

EXAMPLE 10 the compound utilized as an initiator in Example 9 is only slightly soluble in typical coating solvents. To establish the effects of blending vs. those obtained in a polymerization coating, 0.8 g of compound (9) was used in one case as the initiator of n-vinyl-carbazole polymerization, and in the other as simply the acceptor in a polyvinylcarbazole formulation. For the blending formulation, the acceptor was roller milled with a THF solution containing 10 g of commercial polyvinylcarbazole. The mixture, after two days, was filtered and coated onto an identical substrate as was the polymerization formulation of Example 9. The physical properties were essentially the same in either case. A comparison of the electrophotographic properties is given below:

|  | charge acceptance (volts) | dark decay (volts/sec) | exposure to t1/3 μJ/cm² | residual voltage |
| --- | --- | --- | --- | --- |
| 10% polyvinyl-carbazole blend | + 480 | 1 | 220 | 35 |
|  | − 410 | 1 | 270 | 30 |
| Polymerized N-vinyl carbazole with (9) | + 650 | 6 | 91 | 50 |
|  | − 700 | 3 | 139 | 50 |

These data show that the polymerization process involving the initiator-acceptor compound provides a coating formulation which is about three times as fast toward positive corona as the blending formulation.

EXAMPLE 11

The procedure of Example 4 was followed using the initiator (10) and the monomer N-vinylcarbazole in the ratio initiator/monomer=1.0 g/10 g. The polymerization occurred about two seconds after the mixture melted. A filtered 100 ml of the reaction products gave a tough transparent coating of high photopic transmission. Its electrophotographic properties toward tungsten illumination were:

1. positive charge acceptance=500 volts, dark decay=4 volts/sec., exposure required to t1/3 of the decay curve=105 μJ/cm², residual voltage=50 volts.

2. negative charge acceptance=650 volts, dark decay=4 volts/sec., exposure required to t1/3 of the decay curve=228 μJ/cm², residual voltage=40 volts.

Positive corona in a commercial copy machine was used to make several copies from a plate coated with this formulation.

EXAMPLE 12

The procedure of Example 4 was followed using the initiator (8) and the monomer N-vinylcarbazole in the ratio initiator/monomer=0.4 g/10 g. The polymerization occurred about ten minutes after the mixture melted. The reaction mixture was taken up in THF, filtered, and coated onto an aluminum substrate. The light yellow coating had good adhesion and very high photopic transmission. A solution blend of this acceptor and polyvinylcarbazole could not be prepared due to the high insolubility of the acceptor compound. The fact that the polymerization mixture shows photoconductivity of moderate measure indicates a different mechanism in the photoconduction between the polymerization reaction products and the charge transfer products from blending. The electrophotographic properties of the coating from the N-vinylcarbazole polymerization, using tungsten illumination, were:

1. positive charge acceptance=650 volts, dark decay=6.6 volts/sec., exposure required to t1/3 of the decay curve=950 μJ/cm², residual voltage=60 volts.

2. negative charge acceptance=600 volts, dark decay=10 volts/sec., exposure required to t1/3 of the decay curve=917 μJ/cm², residual voltage=50 volts.

The exposure to t1/3, with the use of the 80B filter, required 100 μJ/cm² less than the above values.

EXAMPLE 13

In order to test the effect on the polymerization of N-vinylcarbazole and the photoconductivity of the possible reaction mixture, from compounds in these classes having auxiliary ligands other than fluorine, compound (5) was used as the initiator. A 10 g portion of N-vinylcarbazole and 0.4 g of compound (5) were intimately mixed and set up for the polyermization reaction as in Example 4. Twenty minutes after melting, and while being maintained at a temperature of about 80° C., the reaction mass became viscous enough to cause the stirrer button to freeze, and a few minutes thereafter, the mass solidified. The coating, from THF, exhibited a high photopic transmission, was adhesive, tough, and had the following electrical properties toward tungsten illumination:

1. positive charge acceptance=550 volts, dark decay=2 volts/sec., exposure required to t1/3 of the decay curve=2131 μJ/cm², residual voltage=75 volts.

2. negative charge acceptance=610 volts, dark decay=2 volts/sec., exposure required to t1/3 of the decay curve=1624 μJ/cm², residual voltage=90 volts.

With an 80B filter, to simulate more of a daylight fluorescent illumination, the electrical properties were:

3. positive charge acceptance=640 volts, dark decay=2 volts/sec., exposure required to t1/3 of the decay curve=1279 μJ/cm², residual voltage=75 volts.

4. negative charge addeptance=750 volts, dark decay=2 volts/sec., exposure to t1/3 of the decay curve=1591 μJ/cm², residual voltage=150 volts.

EXAMPLE 14

This example illustrates the catalytic effect of class 1 type compounds toward non-carbazole monomers. The procedure of Example 4 was followed using the compound (3) as the initiator and the monomer 4-vinylpyridine in the ratio initiator/monomer=0.4 g/10 g. The melt took on a red coloration and became viscous after about four hours of heating at about 130° C. A coating from THF producted an extremely tough, adhesive film. The coating did not light decay.

EXAMPLE 15

This example illustrates the catalytic effect of class 11 type compounds toward non-carbazole monomers. The procedure of Example 4 was followed using the compound (9) as the initiator and the monomer 4-vinylbiphenyl in the ratio initiator/monomer=0.4 g/10 g. The melt was maintained at a temperature of 130° C. and after about four hours became viscous. A coating from THF produced a tough, adhesive film. The coating did not light decay.

I claim:

1. A process for polymerizing N-alkenyl carbazoles in the presence of a catalyst to produce organic polymers having sufficiently sensitized photoconductive properties to enable use as an organic photoconductor in the production of photoconductive elements with the catalyst remaining in the polymer comprising heating the carbazole in the presence of a catalyst compound having the general formula

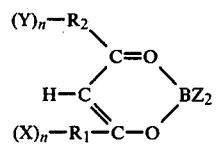

in which X and Y are selected from the group consisting of a halogen, an alkyl or cycloaliphatic group, an aryl or alkaryl group, an alkoxy group and a halogenated methyl derivative, Z is either an aryl group or a halogen group, n is a number from 1 to 5, $R_1$ and $R_2$ are selected from the group consisting of an alkyl or cycloaliphatic group, an aryl or alkaryl group, and in which $R_2$ may be a group having the general formula

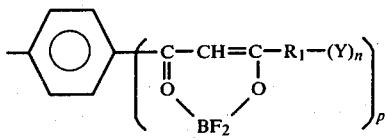

in which $R_1$ has the same meaning as above and p is a number from 1 to 2.

2. A process as claimed in claim 1 in which the alkyl group or the cycloaliphatic group have from 1 to 10 carbon atoms.

3. A process as claimed in claim 1 in which the halogen is fluorine.

4. A process as claimed in claim 1 in which the catalyst component is present in an amount within the range of 0.1 to 20% by weight of the carbazole.

5. A process as claimed in claim 1 in which the polymerization reaction is carried out at a temperature within the range of 60°–200° C.

6. A process as claimed in claim 1 in which the polymerization is carried out as a hot melt of the carbazole and catalyst.

7. A process as claimed in claim 1 in which the polymerization is carried out in the absence of a diluent.

8. A process as claimed in claim 1 in which the alkenyl carbazole is N-vinyl carbazole and analogs thereof.

9. A composition for use in the preparation of photoconductors comprising the polymerization reaction product of the process of claim 1.

10. The process as claimed in claim 1 in which the catalyst has the general formula

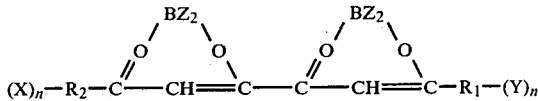

prepared from an oxalate ester.

11. A process for the preparation of 4-vinyl substituted aryl based polymers and copolymers comprising the steps of polymerizing the vinyl based monomers in the presence of a catalyst compound having the general formula

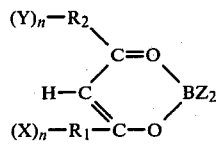

in which X and Y are selected from the group consisting of a halogen, an alkyl or cycloaliphatic group, an aryl or alkaryl group, an alkoxy group and a halogenated methyl derivative, Z is either an aryl group or a halogen group, n is a number from 1 to 5, $R_1$ and $R_2$ are selected from the group consisting of an alkyl or cycloaliphatic group, an aryl or alkaryl group, and in which $R_2$ may be a group having the general formula

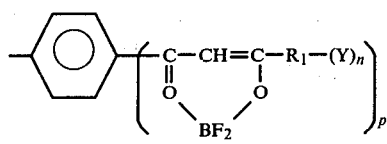

in which $R_1$ has the same meaning as above and p is a number from 1 to 2.

* * * * *

UNITED STATES PATENT OFFICE
CERTIFICATE OF CORRECTION

Patent No. 4,153,769          Dated May 8, 1979

Inventor(s) James M. Halm

It is certified that error appears in the above-identified patent and that said Letters Patent are hereby corrected as shown below:

Col. 5, line 49, delete the numeral "31 10°" and insert -- -10° --.

Signed and Sealed this

Twenty-fifth Day of September 1979

[SEAL]

Attest:

LUTRELLE F. PARKER

*Attesting Officer*     *Acting Commissioner of Patents and Trademarks*